United States Patent [19]

Bobsein

[11] 4,436,948

[45] Mar. 13, 1984

[54] CATALYST COMPOSITIONS

[75] Inventor: Rex L. Bobsein, Bartlesville, Okla.

[73] Assignee: Phillips Petroleum Company, Bartlesville, Okla.

[21] Appl. No.: 415,202

[22] Filed: Sep. 7, 1982

[51] Int. Cl.³ .......................... C07C 2/02; B01J 27/06
[52] U.S. Cl. .................................... 585/532; 585/18; 502/227
[58] Field of Search .................. 585/18, 532; 252/441, 252/442

[56] References Cited

U.S. PATENT DOCUMENTS

| | | | |
|---|---|---|---|
| 2,315,080 | 3/1943 | Reid | 196/10 |
| 2,355,925 | 8/1944 | Reid | 585/532 |
| 2,450,764 | 10/1948 | Meyers et al. | 252/442 |
| 2,899,416 | 8/1959 | Schreyer | 252/442 |
| 2,918,507 | 12/1959 | Kennedy et al. | 585/532 |
| 3,068,306 | 12/1962 | Hay et al. | 585/18 |
| 3,090,821 | 5/1963 | Voltz | 260/683.15 |
| 3,303,239 | 2/1967 | Cleary et al. | 260/683.15 |
| 3,330,883 | 7/1967 | Giannetti et al. | 585/18 |
| 3,770,656 | 11/1973 | Haag et al. | 252/442 |
| 3,798,284 | 3/1974 | Tesei | 260/683.15 D |
| 3,812,036 | 5/1974 | Romine | 585/18 |
| 3,862,257 | 1/1975 | Buben et al. | 260/683.15 D |
| 3,947,507 | 3/1976 | Isa et al. | 252/442 |
| 4,017,553 | 4/1977 | Cesca et al. | 585/532 |
| 4,032,591 | 6/1977 | Cupples et al. | 585/18 |
| 4,048,109 | 9/1977 | Ryu | 252/442 |
| 4,078,010 | 3/1978 | Prillieux et al. | 585/18 |
| 4,113,790 | 9/1978 | Cesca et al. | 260/683.15 B |
| 4,172,855 | 10/1979 | Shubkin et al. | 585/532 |
| 4,214,111 | 7/1980 | Kitamura et al. | 585/532 |

FOREIGN PATENT DOCUMENTS

| | | | |
|---|---|---|---|
| 850910 | 10/1960 | United Kingdom | 252/442 |
| 1047335 | 11/1966 | United Kingdom | 252/442 |

OTHER PUBLICATIONS

J. Grant et al., *Hackh's Chemical Dictionary*, 4th Ed., (1969), pp. 97 and 311.

*Primary Examiner*—Delbert E. Gantz
*Assistant Examiner*—Cynthia A. Prezlock

[57] ABSTRACT

The oligomerization of olefins to give lube oil range products can be improved by the use of a catalyst containing a Group IIIA metal and one or more metals from Group IV.

11 Claims, No Drawings

CATALYST COMPOSITIONS

BACKGROUND

The oligomerization of hydrocarbons to produce synthetic lubricants has shown promise as an alternative to the current use of mineral oils. Synthetic lubricants will have molecular weights and other properties within defined limits so that their suitability for their intended uses can be assured.

THE INVENTION

The invention deals with the catalytic oligomerization of 1-olefins to produce oligomers, which oligomers have utility as lube oil components.

In one embodiment, 1-decene is polymerized in the presence of a catalyst containing aluminum chloride and zirconium or hafnium chloride in about a 1 to 1 molar ratio. The product contains a high percentage of $C_{30}$–$C_{40}$ oligomers which, when hydrogenated, are useful as motor oils.

ADVANTAGES

In accordance with the invention, the oligomerization of olefins can be effected with certain advantages. They include:
(1) high selectivity to $C_{30}$–$C_{40}$ oligomers, and
(2) high conversion of 1-decene to products.

OBJECTS OF THE INVENTION

It is one object of the invention to produce a composition which is useful as a catalyst for the oligomerization of olefins.

It is another object of the invention to make a catalyst composition which, when used to oligomerize olefins, yields a high selectivity to highly desired oligomers useful as motor oils after hydrogenation.

It is still another object of the invention to carry out a process in which olefins are catalytically oligomerized to produce oligomers whose molecular weights are within a desired range.

It is a further object of the invention to produce synthetic lubricants containing the oligomers produced using the catalyst composition and catalytic oligomerization process of the invention.

DESCRIPTION OF THE INVENTION

Catalyst Compositions

The catalysts of the invention contain at least two metal-halide components. The first component contains one or more metals from Group IIIA and the second contains one or more metals from Group IVB and optionally one or more from Group IVA of the Periodic Table. The halides include fluoride, chloride, bromide, and iodide.

The Group IIIA metal halides useful in the invention include aluminum, gallium, and indium halides. Aluminum chloride is preferred for use as the first component. Mixtures of metal halide-containing materials are contemplated.

The Group IV metal halides useful in the second component include the metal halides of Group IVB of the Periodic Table. Among the suitable Group IVB metal halides are titanium, zirconium, and hafnium halides. Combinations of any of the group IVB metal halides can be employed.

In one embodiment aluminum and zirconium halides are combined in a catalyst.

In another, an aluminum halide is used with a hafnium halide.

The atomic ratios of metals present in the catalyst of the invention has a bearing on their effectiveness in the production of oligomers. It has been found that for binary catalysts, i.e., those containing only Group IIIA and IVB metals, the above ratio of the first component to the second should be between about 0.9:1 to 1.1:1. Accordingly, a composition containing aluminum and zirconium would have an Al/Zr atomic ratio ranging from about 0.9:1 to 1.1:1. A ratio of 1:1 is preferred.

Olefins

The monomers to be oligomerized in accordance with the invention are 1-olefins. Generally, they will contain between about 2 and 20 carbon atoms, with olefins having 6 to 16 carbon atoms preferred. 1-Decene is highly preferred. Mixtures of monomers can be used.

While the use of aliphatic olefins as reactants favors the production of long chain oligomers, there may be some branching present in the monomer reactant. The percentage of branching which is tolerable is generally any amount which will not be detrimental to either the oligomerization of the monomer mixture or to the final properties of the oligomers which are desired.

Although the discussion above uses the term "monomers", the use of one or more low molecular weight polymerization products as reactants is contemplated.

Reaction Conditions

The conditions under which the catalyst composition and unsaturated reactant are contacted are critical. Oxygen and moisture must be excluded from the reactants. Solvent is necessary as a heat sink. This discussion is merely suggestive of possible guidelines for the artisan. Useful parameters depend to a large extent on the particular reactants and catalysts being employed.

Useful temperatures for the oligomerization lie between about 0° C. and 200° C., with 50° C. to 120° C. preferred.

Useful reaction times range from 1 minute to 5 days, with 1 hour preferred.

Products

When the catalyst system of this invention is used, the oligomerization of olefins produces a high yield of relatively low molecular weight molecules. In one embodiment, 1-decene is polymerized in the presence of aluminum and zirconium chlorides to produce a high percentage of $C_{30}$ to $C_{40}$ oligomers.

The utilities of the oligomers made according to the invention depends upon the properties of the oligomerized products. The properties of $C_{30}$ to $C_{40}$ oligomers after hydrogenation make them suitable for use as motor oil lubricants. In addition to their use as synthetic lubricants the products of the invention also have utility as waxes and as plasticizing agents for polymers.

EXAMPLES

EXAMPLE I

Oligomerization reactions were run in a 250 mL 3-necked round-bottom flask fitted with magnetic stirrer and a reflux condenser. An argon bubbler attached to the top of the condenser provided inert atmosphere. All reactions were run at 98° C., reflux temperature of the heptane solvent. 1-Decene and heptane were added to the reactor along with the catalyst.

Procedure for run #1 is given as an example: 0.379 g AlCl$_3$ (2.8 mmole), 0.621 g ZrCl$_4$ (2.7 mmole) (Al/Zr atom ratio 1.06), 8.0 g 1-decene and 80 mL n-heptane were combined under argon in the flask, heated to reflux for 1 hr, then cooled to ambient temperature. The mixture was then filtered to remove catalyst. The filtrate was washed three times with 10% NH$_4$OH (100 mL total), twice with water, then dried over 3A molecular sieves. Solvent was removed on a rotary evaporator. The resultant product was analyzed with a gas chromatograph with a flame ionization detector. Typical results are shown in Table I.

TABLE I

| Run # | Catalyst | Al/Zr Ratio | % Conversion[a] | % Selectivity[b] to C$_{30}$ and C$_{40}$ |
|---|---|---|---|---|
| 1 | AlCl$_3$/ZrCl$_4$ | 1.06 | 93 | 51 |
| 2 | " | 1.05 | 90 | 49 |
| 3 | " | 1.06 | 88 | 51 |
| 4 | " | 0.11 | 93 | 45 |
| 5 | " | 9.8 | 94 | 48 |
| 6 | AlCl$_3$ only | — | 94 | 34 |
| 7 | ZrCl$_4$ only | — | 97 | 38 |

[a]Conversion means percent 1-decene converted
[b]Selectivity means percent product converted to C$_{30}$-C$_{40}$ oligomers.

The data show that the combination of Al and Zr chlorides markedly improves selectivity to lube oil range oligomers. Also the data show that a 1:1 atom ratio significantly improves selectivity.

The data demonstrate that at Zr/Al ratios near 1, the selectivity to C$_{30}$-C$_{40}$ product is much higher than that for a higher ratio or for either metal alone.

EXAMPLE II

1-Decene was diluted and oligomerized as recited above, substituting the catalysts shown in Table II.

TABLE II

| Catalyst | Al/Hf ratio | % Conversion | % Selectivity |
|---|---|---|---|
| AlCl$_3$ | — | 94 | 34 |
| AlCl$_3$—HfCl$_3$ | 1:1 | 92 | 48 |
| " | 1:1 | 95 | 45 |
| " | 10:1 | 98 | 29 |
| " | 1:10 | 98 | 32 |

This table shows improved selectivity using AlCl$_3$—HfCl$_3$ in about a 1:1 atom ratio.

Reasonable variations, such as would occur to the skilled artisan, can be made in the invention without departing from the scope thereof.

I claim:

1. A catalyst composition suitable for use in the oligomerization of olefins comprising at least two metal containing components wherein:
   the first component contains one or more Group IIIA metal halides and the second component contains one or more metal halides selected from Group IVB metals and the catalyst contains metal components in about equal amounts based on their atomic weights.

2. The catalyst of claim 1 wherein the first component contains aluminum halide.

3. The catalyst of claim 2 wherein the second component is zirconium halide.

4. The catalyst of claim 2 wherein the second component is hafnium halide.

5. The catalyst of any one of claims 1-4 wherein the ratio of the first component to the second component is between 0.9 to 1 to 1.1 to 1.

6. A process of oligomerizing olefins comprising subjecting them to oligomerization conditions in the presence of a catalyst containing:
   (1) a Group IIA metal halide, and
   (2) at least one other metal halide selected from Group IVB metals, wherein the catalyst contains metal components in about equal amounts based on their atomic weights.

7. The process of claim 6 wherein component (1) contains aluminum.

8. The process of claim 7 wherein component (2) contains zirconium.

9. The process of claim 7 wherein component (2) contains hafnium.

10. The process of any one of claims 6-9 wherein the ratio of the first component to the second component is between 0.9 to 1 to 1.1 to 1.

11. The process of claim 6 wherein the oligomerization product contains a high percentage of C$_{30}$-C$_{40}$ oligomers.

* * * * *